(12) United States Patent
Chen et al.

(10) Patent No.: US 9,040,037 B2
(45) Date of Patent: May 26, 2015

(54) **CULTURE MEDIUM FOR *LACTOBACILLUS ACIDOPHILUS* AND *STREPTOCOCCUS FAECALIS*, COMPOSITION COMPRISING THE SAME AND PREPARATION METHOD THEREOF**

(75) Inventors: Binhua Chen, Shanghai (CN); Xuesong Wang, Shanghai (CN); Liang Zhang, Shanghai (CN)

(73) Assignee: Shanghai Sine Pharmaceutical Laboratories Co., Ltd., Shanghai (CN)

( * ) Notice: Subject to any disclaimer, the term of this patent is extended or adjusted under 35 U.S.C. 154(b) by 990 days.

(21) Appl. No.: 12/527,104

(22) PCT Filed: Feb. 3, 2008

(86) PCT No.: PCT/CN2008/070255
§ 371 (c)(1),
(2), (4) Date: Aug. 13, 2009

(87) PCT Pub. No.: WO2008/101428
PCT Pub. Date: Aug. 28, 2008

(65) Prior Publication Data
US 2010/0119487 A1    May 13, 2010

(30) Foreign Application Priority Data
Feb. 16, 2007   (CN) .......................... 2007 1 0037649

(51) Int. Cl.
*A01N 63/00*   (2006.01)
*C12N 1/00*    (2006.01)
*C12N 1/20*    (2006.01)
*A23L 1/30*    (2006.01)
*C12N 1/04*    (2006.01)

(52) U.S. Cl.
CPC ................ *C12N 1/20* (2013.01); *A23L 1/3014* (2013.01); *A23V 2002/00* (2013.01); *A23Y 2220/03* (2013.01); *A23Y 2240/33* (2013.01); *A23Y 2300/55* (2013.01); *A61K 35/744* (2013.01); *A61K 35/745* (2013.01); *A61K 35/747* (2013.01); *C12N 1/04* (2013.01); *Y10S 435/853* (2013.01); *Y10S 435/854* (2013.01); *Y10S 435/885* (2013.01)

(58) Field of Classification Search
None
See application file for complete search history.

(56) References Cited

U.S. PATENT DOCUMENTS

| | | | |
|---|---|---|---|
| 4,147,773 A | 4/1979 | Ogasa | |
| 6,368,591 B1 * | 4/2002 | Chen et al. ................. | 424/93.45 |

FOREIGN PATENT DOCUMENTS

| | | |
|---|---|---|
| CN | 1103584 A | 6/1995 |
| CN | 1223865 A | 7/1999 |
| CN | 1228018 A | 9/1999 |
| JP | 2002-142719 A | 5/2002 |
| JP | 2003-171292 A | 6/2003 |

OTHER PUBLICATIONS

Fang et al. "Identification of Anaerobe using Gas Chromatography," Microbiology, No. 6, 1989, pp. 434-347.
Fang et al. "Identification of Anacrobe using Gas Chromatography," Microbiology, No. 6, 1989, pp. 434-347.

* cited by examiner

*Primary Examiner* — Vera Afremova
(74) *Attorney, Agent, or Firm* — Hamre, Schumann, Mueller & Larson, P.C.

(57) ABSTRACT

The present invention provides a triple vital bacteria composition, including: powder of *Bifidobacterium longum*, powder of *Lactobacillus acidophilus*, and powder of *Streptococcus faecalis*. The present invention further provides a method for preparing the above triple vital bacteria composition, as well as the protection agents, the fermenting culture medium and the seed culture medium used therein.

9 Claims, No Drawings

CULTURE MEDIUM FOR *LACTOBACILLUS ACIDOPHILUS* AND *STREPTOCOCCUS FAECALIS*, COMPOSITION COMPRISING THE SAME AND PREPARATION METHOD THEREOF

TECHNICAL FIELD

The present invention relates to a triple vital bacteria composition comprising three vital and beneficial bacteria and preparation method thereof, in particular to a triple vital bacteria composition comprising *Bifidobacterium longum*, *Lactobacillus acidophilus* and *Streptococcus faecalis* and preparation method thereof.

BACKGROUND ART

*Bifidobacterium*, *Lactobacillus acidophilus* and *Streptococcus faecalis* are important members of normal flora in human and animal, and they are collectively adhered to the lower intestinal mucous membrane and can advantageously affect the body. They can prevent entrance of external pathogenic bacteria, and their metabolites can provide necessary vitamins to host. They participate and assist digestion and adsorption of nourishment. The above bacterial can activate immunological function of body, and reduce adsorption of enterogenous toxin. The *Bifidobacterium* will be reduced gradually, due to digestive system diseases, use of abundant antibiotics and increase of age. In order to keep the normal level of the above beneficial bacterial, a formulation containing these bacteria have been studied. For example, Chinese Patent CN1103584 has disclosed an oral solution comprising three bacteria, which comprised *Bifidobacterium*, *Lactobacillus acidophilus* and *Streptococcus faecalis*, and its preparation method. However, this oral solution has a poor stability. The survival rate of these bacteria is low, thereby it cannot be conserved for a long term.

Chinese Patent CN1119154C has disclosed a triple vital bacteria composition comprising three vital and beneficial bacteria and its preparation method. This patent proposed to use a special protection agent to increase the stability of *Bifidobacterium*, *Lactobacillus acidophilus* and *Streptococcus faecalis*. Although the above protection agent can increase the stability of *Bifidobacterium*, *Lactobacillus acidophilus* and *Streptococcus faecalis* in a way, it is unsatisfied on further increase of the stability.

In addition, no references has proposed to improve the seed culture mediums and fermentation culture mediums of *Bifidobacterium*, *Lactobacillus acidophilus* and *Streptococcus faecalis* to increase the stability of *Bifidobacterium*, *Lactobacillus acidophilus* and *Streptococcus faecalis*.

Therefore, there is a need to provide a triple vital bacteria composition comprising three vital and beneficial bacteria which has higher stability.

SUMMARY OF INVENTION

The object of the present invention is to provide a new triple vital bacteria composition comprising three vital and beneficial bacteria which has higher stability.

Another object of the present invention is to provide a method for preparing the above triple vital bacteria composition comprising three vital and beneficial bacteria, which can easily produce the above triple vital bacteria composition.

In one aspect, the present invention provides a triple vital bacteria composition, including:

powder of *Bifidobacterium longum*,
powder of *Lactobacillus acidophilus*, and
powder of *Streptococcus faecalis*,
wherein the powder of *Bifidobacterium longum* comprises *Bifidobacterium longum* and a first protection agent, wherein the first protection agent includes 8-50% of defatted milk powder, 0.01-10% of sodium glutamate, 8-50% of isolactose, 0.01-5% of Vc-Na and 5-30% of starch, based on the total weight of the first protection agent,
wherein the powder of *Lactobacillus acidophilus* comprises *Lactobacillus acidophilus* and a second protection agent and the powder of *Streptococcus faecalis* comprises *Streptococcus faecalis* and a second protection agent, and the second protection agent includes 6-70% of defatted milk powder, 0.01-10% of sodium gultamate, 8-50% of isolactose, 0.01-5% of Vc-Na and 4-30% of starch, based on the total weight of the second protection agent.

In another aspect, the present invention provides an agent protection agent, comprising 6-70% of defatted milk powder, 0.1-10% of sodium gultamate, 8-50% of isolactose, 0.01-5% of Vc-Na and 4-30% of starch, based on the total weight of the protection agent.

The present invention further provides a method for preparing the above triple vital bacteria composition, comprising the following steps:

(a) inoculating *Bifidobacterium longum* in a first seed culture medium to obtain an inoculated product of *Bifidobacterium longum*;

(b) inoculating *Lactobacillus acidophilus* in a second seed culture medium to obtain an inoculated product of *Lactobacillus acidophilus*;

(c) inoculating *Streptococcus faecalis* in a second seed culture medium to obtain an inoculated product of *Streptococcus faecalis*;

(d) fermenting the inoculated product of *Bifidobacterium longum* obtained from step (a) in a first fermentation culture medium to obtain a fermentation product of *Bifidobacterium longum*;

(e) fermenting the inoculated product of *Lactobacillus acidophilus* obtained from step (b) in a second fermentation culture medium to obtain a fermentation product of *Lactobacillus acidophilus*;

(f) fermenting the inoculated product of *Streptococcus faecalis* obtained from step (c) in a second fermentation culture medium to obtain a fermentation product of *Streptococcus faecalis*;

(g) mixing *Bifidobacterium longum* with a first protection agent and then freeze-drying to obtain powder of *Bifidobacterium longum*;

(h) mixing *Lactobacillus acidophilus* and *Streptococcus faecalis* with a second protection agent, respectively and then freeze-drying to obtain powder of *Lactobacillus acidophilus* and powder of *Streptococcus faecalis*;

(i) mixing the above powder of *Bifidobacterium longum*, powder of *Lactobacillus acidophilus* and powder of *Streptococcus faecalis* to obtain a triple vital bacteria composition.

In one preferred embodiment according to the present invention, the first seed culture medium comprises 1.1-6.5% by weight of nitrogen source, 0.5-3% by weight of carbon source, 0.6-1.5% by weight of nutritious material, 0.15-5% by weight of mineral salt and 84.00-97.65% by weight of solvent.

In another preferred embodiment according to the present invention, the second seed culture medium comprises 1.1-6.5% by weight of nitrogen source, 0.2-3% by weight of carbon source, 0.5-25% by weight of nutritious material, and 65.5-98.2% by weight of solvent, In another preferred embodiment according to the present invention, the first fermentation culture medium comprises 1.1-6.5% by weight of nitrogen source, 0.5-3% by weight of carbon source, 0.6-1.5% by weight of nutritious material, 0.15-5% by weight of mineral salt and 84.00-97.65% by weight of solvent.

In another preferred embodiment according to the present invention, the second fermentation culture medium comprises 1.1-6.5% by weight of nitrogen source, 0.2-3% by weight of carbon source, 0.5-25% by weight of nutritious material, and 65.5-98.2% by weight of solvent.

The present invention further provides seed culture medium comprising 1.1-6.5% by weight of nitrogen source, 0.2-3% by weight of carbon source, 0.5-25% by weight of nutritious material, and 65.5-98.2% by weight of solvent.

The present invention further provides a fermentation culture medium comprising 1.1-6.5% by weight of nitrogen source, 0.2-3% by weight of carbon source, 0.5-25% by weight of nutritious material, and 65.5-98.2% by weight of solvent.

The present invention further provides use of the above triple vital bacteria composition in treating constipation.

The fermentation liquid according to the present invention can increase the yield of the bacteria. The protection agents used during freeze-drying can increase greatly the survival rate of the bacteria. The formulation prepared by the freeze-dried powder of the bacteria can prolong the survival rate of the bacteria and increase the stability of the formulation.

DETAILED DESCRIPTION OF THE INVENTION

Triple Vital Bacteria Composition Comprising Three Vital and Beneficial
Bacteria In one aspect, the present invention provides a triple vital bacteria composition, including:
powder of *Bifidobacterium longum*,
powder of *Lactobacillus acidophilus*, and
powder of *Streptococcus faecalis*,
wherein the powder of *Bifidobacterium longum* comprises *Bifidobacterium longum* and a first protection agent, wherein the first protection agent includes 8-50% of defatted milk powder, 0.01-10% of sodium glutamate, 8-50% of isolactose, 0.01-5% of Vc-Na and 5-30% of starch, based on the total weight of the first protection agent.

wherein the powder of *Lactobacillus acidophilus* comprises *Lactobacillus acidophilus* and a second protection agent and the powder of *Streptococcus faecalis* comprises *Streptococcus faecalis* and a second protection agent, and the second protection agent includes 6-70% of defatted milk powder, 0.01-10% of sodium gultamate, 8-50% of isolactose, 0.01-5% of Vc-Na and 4-30% of starch, based on the total weight of the second protection agent.

*Bifidobacterium longum, Lactobacillus acidophilus* and *Streptococcus faecalis* in the present invention are conventional, and they have been disclosed in granted U.S. Pat. No. 6,368,591, in which *Bifidobacterium longum* has a deposit number of CCTCC M98003, *Lactobacillus acidophilus* has a deposit number of CCTCC M98004, and *Streptococcus faecalis* has a deposit number of CCTCC 98005.

The *Bifidobacterium longum* is an anaerobe. Gram's stain of *Bifidobacterium longum* is positive but inhomogeneous. The strain has neither spore nor capsule nor flagellum; the mycelia are straight or curved or Y-, V- and stick type. In one preferred embodiment according to the present invention, the *Bifidobacterium longum* is *Bifidobacterium longum* 6-1 (CCTCC M98003).

*Lactobacillus acidophilus* is a facultative anaerobe. Gram's strain of *Lactobacillus acidophilus* is positive. The strain has neither spore, nor capsule nor flagellum. The mycelia are short stick-like or ball stick-like with blunt round at two ends of stick-like mycelia and are arranged in single or twin form. In one preferred embodiment according to the present invention, the *Lactobacillus acidophilus* is *Lactobacillus acidophilus* YIT2004 (CCTCC M98004).

*Streptococcus faecalis* is an facultative anaerobe. Gram's stain of *Streptococcus faecalis* is positive. The strain has neither spore, capsule, nor flagellum. The mycelia are egg round, in most cases arranged in twin form, and also arranged in short chain form. In one preferred embodiment according to the present invention, the *Streptococcus faecalis* is *Streptococcus faecalis* YIT0027 (CCTCC M98005)

Protection Agent

The first protection agent in the present invention is conventional. A skilled person in the art can determine which protection agent can be used in the present invention according to the common knowledge in the art, for example, see CN11191540. In one preferred embodiment according to the present invention, the first protection agent comprises 8-50% of defatted milk powder, 0.01-10% of sodium glutamate, 8-50% of isolactose, 0.01-5% of Vc-Na and 5-30% of starch, based on the total weight of the first protection agent. In another preferred embodiment according to the present invention, the defatted milk powder has an amount of 10-40%, preferably 15-35%, more preferably 20-30%, most preferably 22-28%, based on the total weight of the first protection agent. In another preferred embodiment according to the present invention, the sodium glutamate has an amount of 0.1-8%, preferably 0.5-5%, more preferably 1-3%, most preferably 1.5-2.5%, based on the total weight of the first protection agent. In another preferred embodiment according to the present invention, the isolactose has an amount of 10-45%, preferably 15-35%, more preferably 20-30%, most preferably from 22-25%, based on the total weight of the first protection agent. In another preferred embodiment according to the present invention, the Vc-Na has an amount of 0.1-4%, preferably 0.5-3%, more preferably 1-2.5%, most preferably 1.5-2%, based on the total weight of the first protection agent. In another preferred embodiment according to the present invention, the starch has an amount of 8-25%, preferably 10-20%, more preferably 12-18%, most preferably 13-17%, based on the total weight of the first protection agent.

The second protection agent in the present invention comprises 6-70% of defatted milk powder, 0.01-10% of sodium gultamate, 8-50% of isolactose, 0.01-5% of Vc-Na and 4-30% of starch, based on the total weight of the second protection agent. In another preferred embodiment according to the present invention, the defatted milk powder has an amount of 10-60%, preferably 20-50%, more preferably 30-40%, most preferably 33-37%, based on the total weight of the second protection agent. In another preferred embodiment according to the present invention, the sodium gultamate has an amount of 0.1-8%, preferably 0.5-5%, more preferably 1-3%, most preferably 1.5-2.5%, based on the total weight of the second protection agent. In another preferred embodiment according to the present invention, the isolactose has an amount of 10-45%, preferably 15-35%, more preferably 20-30%, most preferably 22-25%, based on the total weight of the second protection agent. In another preferred embodiment according to the present invention, the Vc-Na has an amount of 0.1-4%, preferably 0.5-3%, more preferably 1-2.5%, most preferably 1.5-2%, based on the total weight of the second protection agent. In another preferred embodiment according to the present invention, the starch has an amount of 5-25%, preferably 10-20%, more preferably 12-18%, most preferably 13-17%, based on the total weight of the second protection agent.

In one preferred embodiment according to the present invention, the second protection agent consists of:

| Defatted milk powder | sodium gultamate | Isolactose | Vc-Na | Starch |
|---|---|---|---|---|
| 2 parts by weight | 0.5 parts by weight | 2.5 parts by weight | 0.2 parts by weight | 1 part by weight |

The defatted milk powder in the present invention is conventional. A skilled person in the art can determine according to the prior art which defatted milk powder can be used in the present invention. In one preferred embodiment according to the present invention, the defatted milk powder is a commercial defatted milk powder.

The sodium gultamate in the present invention is conventional. A skilled person in the art can determine according to the prior art which sodium gultamate can be used in the present invention. In one preferred embodiment according to the present invention, the sodium gultamate is a commercial sodium gultamate.

The isolactose in the present invention is conventional. A skilled person in the art can determine according to the prior art which isolactose can be used in the present invention. In one preferred embodiment according to the present invention, the isolactose is a commercial isolactose.

The Vc-Na in the present invention is conventional. A skilled person in the art can determine according to the prior art which Vc-Na can be used in the present invention. In one preferred embodiment according to the present invention, the Vc-Na is a commercial Vc-Na.

The starch in the present invention is conventional. A skilled person in the art can determine according to the prior art which starch can be used in the present invention. In one preferred embodiment according to the present invention, the starch is a commercial starch.

Method for Producing a Triple Vital Bacteria Composition Comprising Three Vital and Beneficial Bacteria The present invention on the other hand provides a method for preparing the above triple vital bacteria composition, comprising the following steps:

(a) inoculating *Bifidobacterium longum* in a first seed culture medium to obtain an inoculated product of *Bifidobacterium longum*;

(b) inoculating *Lactobacillus acidophilus* in a second seed culture medium to obtain an inoculated product of *Lactobacillus acidophilus*;

(c) inoculating *Streptococcus faecalis* in a second seed culture medium to obtain an inoculated product of *Streptococcus faecalis*;

(d) fermenting the inoculated product of *Bifidobacterium longum* obtained from step (a) in a first fermentation culture medium to obtain a fermentation product of *Bifidobacterium longum*;

(e) fermenting the inoculated product of *Lactobacillus acidophilus* obtained from step (b) in a second fermentation culture medium to obtain a fermentation product of *Lactobacillus acidophilus*;

(f) fermenting the inoculated product of *Streptococcus faecalis* obtained from step (c) in a second fermentation culture medium to obtain a fermentation product of *Streptococcus faecalis*;

(g) mixing *Bifidobacterium longum* with a first protection agent and then freeze-drying to obtain powder of *Bifidobacterium longum*;

(h) mixing *Lactobacillus acidophilus* and *Streptococcus faecalis* with a second protection agent, respectively, and then freeze-drying to obtain powder of *Lactobacillus acidophilus* and powder of *Streptococcus faecalis*;

(i) mixing the above powder of *Bifidobacterium longum*, powder of *Lactobacillus acidophilus* and powder of *Streptococcus faecalis* to obtain a triple vital bacteria composition.

In the above step (a), the method of inoculating *Bifidobacterium longum* is conventional. A skilled person in the art can know according to the prior art how to inoculate the *Bifidobacterium longum*. The method of inoculation can be seen from CN1119145C. In one preferred embodiment according to the present invention, the method of inoculation comprises flame-inoculation, i.e., clamping cotton with alcohol with a nipper; igniting the cotton and burning it around inoculation head of the seed tank up and down, thereby sterilizing with a flame. Then, the cover of the inoculation head of the seed tank is turned on, and a rubber tube equipped with the seed inoculation bottle is inserted rapidly into the inoculation head under flame. The valve of the inoculation opening is opened slowly, and the seed is poured into the tank.

In the above step (b), the method of inoculating *Lactobacillus acidophilus* is conventional. A skilled person in the art can know according to the prior art how to inoculate the *Lactobacillus acidophilus*. The method of inoculation can be seen from CN11191415C. In one preferred embodiment according to the present invention, the method of inoculation comprises flame-inoculation, i.e., clamping cotton with alcohol with a nipper; igniting the cotton and burning it around inoculation head of the seed tank up and down, thereby sterilizing with a flame. Then, the cover of the inoculation head of the seed tank is turned on, and a rubber tube equipped with the seed inoculation bottle is inserted rapidly into the inoculation head under flame. The valve of the inoculation opening is opened slowly, and the seed is poured into the tank.

In the above step (c), the method of inoculating *Streptococcus faecalis* is conventional. A skilled person in the art can know according to the prior art how to inoculate the *Streptococcus faecalis*. The method of inoculation can be seen from CN1119145C. In one preferred embodiment according to the present invention, the method of inoculation comprises flame-inoculation, i.e., clamping cotton with alcohol with a nipper; igniting the cotton and burning it around inoculation head of the seed tank up and down, thereby sterilizing with a flame. Then, the cover of the inoculation head of the seed tank is turned on, and a rubber tube equipped with the seed inoculation bottle is inserted rapidly into the inoculation head under flame. The valve of the inoculation opening is opened slowly, and the seed is poured into the tank.

In the above step (d), the method of fermenting the inoculated product of *Bifidobacterium longum* is conventional. A skilled person in the art can know according to the disclosure of the present application in combination with the prior art how to ferment the inoculated product of *Bifidobacterium longum*. The method of fermenting can be seen from CN11199145C. In one preferred embodiment according to the present invention, the method of fermenting comprises liquid culture method (i.e., the culture medium used is one or more aqueous solution, such as peptone solution and nutrient broth), solid culture method (i.e., the culture medium is a medium comprising solid material such as agar and gelatin, in a form of solid or semi-solid).

In the above step (e), the method of fermenting the inoculated product of *Lactobacillus acidophilus* is conventional. A skilled person in the art can know according to the disclosure of the present application in combination with the prior art how to ferment the inoculated product of *Lactobacillus acidophilus*. The method of fermenting can be seen from CN111991450. In one preferred embodiment according to the present invention, the method of fermenting comprises liquid culture method (i.e., the culture medium used is one or more aqueous solution, such as peptone solution and nutrient broth), solid culture method (i.e., the culture medium is a medium comprising solid material such as agar and gelatin, in a form of solid or semi-solid).

In the above step (f), the method of fermenting the inoculated product of *Streptococcus faecalis* is conventional. A skilled person in the art can know according to the disclosure of the present application in combination with the prior art how to ferment the inoculated product of *Streptococcus faecalis*. The method of fermenting can be seen from CN11199145C. In one preferred embodiment according to the present invention, the method of fermenting comprises liquid culture method (i.e., the culture medium used is one or more aqueous solution, such as peptone solution and nutrient broth), solid culture method (i.e., the culture medium is a medium comprising solid material such as agar and gelatin, in a form of solid or semi-solid).

In the above steps (g) and (h), the method of freeze-drying is conventional. A skilled person in the art can know according to the disclosure of the present application in combination with the prior art how to freeze-dry. The method of freeze-drying can be seen from CN1119145C. In one preferred embodiment according to the present invention, the method of freeze-drying comprises a process of freeze-drying under a low temperature, i.e., removing water and other solvents from the frozen biologics by sublimation. The sublimation means the process in which the solvent such as water directly changes from solid to gas without experiencing a liquid state, like dry ice.

First Seed Culture Medium

The first seed culture medium in the above step (a) is conventional. A skilled person in the art can determine according to the prior art which seed culture medium can be used to ferment *Bifidobacterium longum*. The first seed culture medium can be seen from "Optimization of Culture Medium of Bifidobacterium longum", Food Industrial Science and Technology, V. 04, 2004.

However, in order to obtain *Bifidobacterium longum* having higher stability, it is preferred to use a specific seed culture medium. In one preferred embodiment according to the present invention, the first seed culture medium comprises 1.1-6.5% by weight of nitrogen source, 0.5-3% by weight of carbon source, 0.6-1.5% by weight of nutritious material, 0.15-5% by weight of mineral salt and 84.00-97.65% by weight of solvent. In another preferred embodiment according to the present invention, the first seed culture medium comprises the following components:

| Formulation of 4000 g | | |
| --- | --- | --- |
| Defatted milk powder | Nitrogen source | 196 g |
| glucose | Carbon source | 58 g |
| Yeast powder | nutritious material | 54 g |
| Ammonia sulfate | Mineral salt | 55 g |
| potassium dihydrogen phosphate | Mineral salt | 12 g |
| dipotassium hydrogen phosphate | Mineral salt | 43 g |
| isolactose | Carbon source | 32 g |
| water | solvent | remaining |

The nitrogen source in the first seed culture medium is conventional. A skilled person in the art can know according to the prior art which nitrogen sources can be used in the present invention. The examples of the nitrogen source can be seen from CN1119154C. In one preferred embodiment according to the present invention, the nitrogen source is one or more selected from the group consisting of defatted milk powder, peptone, tryptone and ammonium salt. In another preferred embodiment according to the present invention, the nitrogen source is one or two selected from the group consisting of defatted milk powder and ammonium sulfate. Generally, based on the total weight of the first seed culture medium, the nitrogen source has an amount of 1.1-6.5% by weight, preferably 1.5-5.5% by weight, more preferably 2.0-5.0% by weight, most preferably 3.0-4.0% by weight.

The carbon source in the first seed culture medium is conventional. A skilled person in the art can deduce according to the disclosure of the present application in combination with the prior art which carbon sources can be used in the present invention. The examples of the carbon sources can be seen from CN1119145C. In one preferred embodiment according to the present invention, the carbon source is one or more selected from the group consisting of glucose, lactose, isolactose, galactose, glycerol, sorbitol, trehalose and maltose. In another embodiment according to the present invention, the carbon source is one or two selected from glucose and isolactose. Generally, based on the total weight of the first seed culture medium, the carbon source has an amount of 0.8-2.8% by weight, preferably 1.0-2.5% by weight, more preferably 1.5-2.0% by weight.

The nutritious material in the first seed culture medium is conventional. A skilled person in the art can know according to the disclosure of the present application in combination with the prior art which nutritious materials can be used in the present invention. The examples of nutritious materials can be seen from CN1119145C. In one preferred embodiment according to the present invention, the nutritious material is yeast powder. Generally, based on the total weight of the first seed culture medium, the nutritious material has an amount of 0.6-1.5% by weight, preferably 0.7-1.2% by weight, more preferably 0.8-1.0% by weight.

The mineral salt (mineral substance) in the first seed culture medium is conventional. A skilled person in the art can know according to the disclosure of the present application in combination with the prior art which mineral salt can be used in the present invention. The examples of the mineral salt can be seen from CN1119145C. In one preferred embodiment according to the present invention, the mineral salt is one or more selected from phosphates. In another preferred embodiment according to the present invention, the mineral salt is one or more selected from the group consisting of potassium dihydrogen phosphate and dipotassium hydrogen phosphate. Generally, based on the total weight of the first seed culture medium, the mineral salt has an amount of 0.15-5% by weight, preferably 0.5-4.5% by weight, more preferably 1.0-3.0% by weight, most preferably 1.5-2.5% by weight.

The solvent in the first seed culture medium is conventional. A skilled person in the art can know according to the disclosure of the present application in combination with the prior art which solvents can be used in the present invention. The examples of the solvents can be seen from CN1119145C. In one preferred embodiment according to the present invention, the solvent is a conventional solvent in the biological culture medium, such as water (pure water).

Second Seed Culture Medium

The second seed culture medium in the above steps (b) and (c) is conventional in the art. A skilled person in the art can determine according to the prior art which seed culture medium can be used to inoculate *Lactobacillus acidophilus* and *Streptococcus faecalis*. The examples of the second seed culture medium can be seen from "*Optimization of Culture Medium of Lactobacillus acidophilus*", Food Industrial Science and Technology V. 06, 2002 and "*Study on fermenting agent of hygienical sour milk to Lactobacillus acidophilus and Streptococcus faecalis*", Journal of Anhui Agricultural Technology Normal College, V01, 2000.

However, in order to obtain *Lactobacillus acidophilus* having higher stability, it is preferred to use a specific seed culture medium. In one preferred embodiment according to the present invention, the second seed culture medium comprises 1.1-6.5% by weight of nitrogen source, 0.2-3% by weight of carbon source, 0.5-25% by weight of nutritious material and 65.5-98.2% by weight of solvent. In another preferred embodiment according to the present invention, the second seed culture medium comprises the following components:

| Formulation of 4000 g | | |
|---|---|---|
| Juice of tomato | nutritious material | 500 g |
| glucose | Carbon source | 60 g |
| Yeast powder | nutritious material | 43 g |
| Tryptone | Nitrogen source | 160 g |
| Peptone | Nitrogen source | 36 g |
| Lactose | Carbon source | 13 g |
| water | solvent | remaining |

The nitrogen source in the second seed culture medium is conventional. A skilled person in the art can know according to the prior art which nitrogen sources can be used in the present invention. The examples of the nitrogen source can be seen from CN1119154C. In one preferred embodiment according to the present invention, the nitrogen source is one or more selected from the group consisting of defatted milk powder, peptone, tryptone and ammonium salt. In another preferred embodiment according to the present invention, the nitrogen source is one or two selected from the group consisting of tryptone and peptone. Generally, based on the total weight of the second seed culture medium, the nitrogen source has an amount of 1.1-6.5% by weight, preferably 1.5-5.5% by weight, more preferably 2.0-5.0% by weight, most preferably 3.0-4.0% by weight.

The carbon source in the second seed culture medium is conventional. A skilled person in the art can determine according to the disclosure of the present application in combination with the prior art which carbon sources can be used in the present invention. The examples of the carbon sources can be seen from CN1119145C. In one preferred embodiment according to the present invention, the carbon source is one or more selected from the group consisting of glucose, lactose, isolactose, galactose, glycerol, sorbitol, trehalose and maltose. In another embodiment according to the present invention, the carbon source is one or two selected from glucose and lactose. Generally, based on the total weight of the second seed culture medium, the carbon source has an amount of 0.5-2.8% by weight, preferably 1.0-2.5% by weight, more preferably 1.5-2.0% by weight.

The nutritious material in the second seed culture medium is conventional. A skilled person in the art can know according to the disclosure of the present application in combination with the prior art which nutritious materials can be used in the present invention. The examples of nutritious materials can be seen from CN1119145C. In one preferred embodiment according to the present invention, the nutritious material is one or more selected from the group consisting of tomato, juice of pickle and yeast powder. In another embodiment according to the present invention, the nutritious material is one or more selected from the group consisting of tomato and yeast powder. Generally, based on the total weight of the second seed culture medium, the nutritious material has an amount of 0.5-25% by weight, preferably 5-20% by weight, more preferably 10-15% by weight.

The solvent in the second seed culture medium is conventional. A skilled person in the art can know according to the disclosure of the present application in combination with the prior art which solvents can be used in the present invention. The examples of the solvents can be seen from CN1119145C. In one preferred embodiment according to the present invention, the solvent is a conventional solvent in the biological culture medium, such as water (pure water).

Fermentation Culture Medium

The first fermentation culture medium in the above step (d) is conventional. A skilled person in the art can know according to the disclosure of the present application in combination with the prior art know which fermentation culture medium can be used to ferment *Bifidobacterium longum*. The examples of the fermentation culture medium can be seen from CN1119145C.

However, in order to obtain *Bifidobacterium longum* having higher stability, it is preferred to use a specific first fermentation culture medium. In one preferred embodiment according to the present invention, the first fermentation culture medium comprises 1.1-6.5% by weight of nitrogen source, 0.5-3% by weight of carbon source, 0.6-1.5% by weight of nutritious material, 0.15-5% by weight of mineral salt and 84.00-97.65% by weight of solvent. In another preferred embodiment according to the present invention, the first fermentation culture medium comprises the following components:

| Formulation of 400 L (400 kg) | | |
|---|---|---|
| Defatted milk powder | Nitrogen source | 20 kg |
| glucose | Carbon source | 9 kg |
| Yeast powder | nutritious material | 6.2 kg |
| Ammonia sulfate | Mineral salt | 2.3 kg |
| potassium dihydrogen phosphate | Mineral salt | 1.1 kg |
| dipotassium hydrogen phosphate | Mineral salt | 2.1 kg |
| Calcium carbonate | Mineral salt | 5.3 kg |
| water | solvent | remaining |

The nitrogen source in the first fermentation culture medium is conventional. A skilled person in the art can know according to the prior art which nitrogen sources can be used in the present invention. The examples of the nitrogen source can be seen from CN1119154C. In one preferred embodiment according to the present invention, the nitrogen source is one or more selected from the group consisting of defatted milk powder, peptone, tryptone and ammonium salt. In another preferred embodiment according to the present invention, the nitrogen source is one or two selected from the group consisting of defatted milk powder and ammonium sulfate. Generally, based on the total weight of the first fermentation culture medium, the nitrogen source has an amount of 1.1-6.5% by weight, preferably 1.5-5.5% by weight, more preferably 2.0-5.0% by weight, most preferably 3.0-4.0% by weight.

The carbon source in the first fermentation culture medium is conventional. A skilled person in the art can determine according to the disclosure of the present application in combination with the prior art which carbon sources can be used in the present invention. The examples of the carbon sources can be seen from CN1119145C. In one preferred embodiment according to the present invention, the carbon source is one or more selected from the group consisting of glucose, lactose, isolactose, galactose, glycerol, sorbitol, trehalose and maltose. In another embodiment according to the present invention, the carbon source is one or two selected from glucose and isolactose. Generally, based on the total weight of the first fermentation culture medium, the carbon source has an amount of 0.8-2.8% by weight, preferably 1.0-2.5% by weight, more preferably 1.5-2.0% by weight.

The nutritious material in the first fermentation culture medium is conventional. A skilled person in the art can know according to the disclosure of the present application in combination with the prior art which nutritious materials can be used in the present invention. The examples of nutritious materials can be seen from CN1119145C. In one preferred embodiment according to the present invention, the nutritious material is yeast powder. Generally, based on the total weight of the first fermentation culture medium, the nutritious material has an amount of 0.6-1.5% by weight, preferably 0.7-1.2% by weight, more preferably 0.8-1.0% by weight.

The mineral salt (mineral substance) in the first fermentation culture medium is conventional. A skilled person in the art can know according to the disclosure of the present application in combination with the prior art which mineral salt can be used in the present invention. The examples of the mineral salt can be seen from CN1119145C. In one preferred embodiment according to the present invention, the mineral salt is one or more selected from phosphates. In another preferred embodiment according to the present invention, the mineral salt is one or more selected from the group consisting of potassium dihydrogen phosphate and dipotassium hydrogen phosphate. Generally, based on the total weight of the first fermentation culture medium, the mineral salt has an amount of 0.15-5% by weight, preferably 0.5-4.5% by weight, more preferably 1.0-3.0% by weight, most preferably 1.5-2.5% by weight.

The solvent in the first fermentation culture medium is conventional. A skilled person in the art can know according to the disclosure of the present application in combination with the prior art which solvents can be used in the present invention. The examples of the solvents can be seen from CN1119145C. In one preferred embodiment according to the present invention, the solvent is conventional solvents in the biological culture medium, such as water (pure water).

The second fermentation culture medium in the above steps (e) and (f) is conventional. A skilled person in the art can know according to the disclosure of the present application in combination with the prior art which fermentation culture medium can be used to ferment *Lactobacillus acidophilus* and *Streptococcus faecalis*.

In one preferred embodiment according to the present invention, the second seed culture medium comprises 1.1-6.5% by weight of nitrogen source, 0.2-3% by weight of carbon source, 0.5-25% by weight of nutritious material and 65.5-98.2% by weight of solvent, the first seed culture medium comprises the following components:

| Formulation of 400 kg | | |
|---|---|---|
| Juice of tomato | nutritious material | 50 kg |
| glucose | Carbon source | 6 kg |
| Yeast powder | nutritious material | 4.3 kg |
| Tryptone | Nitrogen source | 16 kg |
| Peptone | Nitrogen source | 3.6 kg |

-continued

| Formulation of 400 kg | | |
|---|---|---|
| Lactose water | Carbon source solvent | 1.3 kg remaining |

The nitrogen source in the second fermentation culture medium is conventional. A skilled person in the art can know according to the prior art which nitrogen sources can be used in the present invention. The examples of the nitrogen source can be seen from CN1119154C. In one preferred embodiment according to the present invention, the nitrogen source is one or more selected from the group consisting of defatted milk powder, peptone, tryptone and ammonium salt. In another preferred embodiment according to the present invention, the nitrogen source is one or two selected from the group consisting of tryptone and peptone. Generally, based on the total weight of the second fermentation culture medium, the nitrogen source has an amount of 1.1-6.5% by weight, preferably 1.5-5.5% by weight, more preferably 2.0-5.0% by weight, most preferably 3.0-4.0% by weight.

The carbon source in the second fermentation culture medium is conventional. A skilled person in the art can determine according to the disclosure of the present application in combination with the prior art which carbon sources can be used in the present invention. The examples of the carbon sources can be seen from CN1119145C. In one preferred embodiment according to the present invention, the carbon source is one or more selected from the group consisting of glucose, lactose, isolactose, galactose, glycerol, sorbitol, trehalose and maltose. In another embodiment according to the present invention, the carbon source is one or two selected from glucose and lactose. Generally, based on the total weight of the second fermentation culture medium, the carbon source has an amount of 0.5-2.8% by weight, preferably 1.0-2.5% by weight, more preferably 1.5-2.0% by weight.

The nutritious material in the second fermentation culture medium is conventional. A skilled person in the art can know according to the disclosure of the present application in combination with the prior art which nutritious materials can be used in the present invention. The examples of nutritious materials can be seen from CN1119145C. In one preferred embodiment according to the present invention, the nutritious material is one or more selected from the group consisting of tomato, juice of pickle and yeast powder. In another embodiment according to the present invention, the nutritious material is one or more selected from the group consisting of tomato and yeast powder. Generally, based on the total weight of the second fermentation culture medium, the nutritious material has an amount of 0.5-25% by weight, preferably 5-20% by weight, more preferably 10-15% by weight.

The solvent in the second fermentation culture medium is conventional. A skilled person in the art can know according to the disclosure of the present application in combination with the prior art which solvents can be used in the present invention. The examples of the solvents can be seen from CN1119145C. In one preferred embodiment according to the present invention, the solvent is a conventional solvent in the biologic culture medium, such as water (pure water).

In the above steps (g)-(h), the first protection agent and second protection agent are defined as above.

Others

The triple vital bacteria composition according to the present invention can be prepared in various dosage forms, such as oral solution, tablet, capsule, oral disintegrating tablet. In one preferred embodiment according to the present invention, the dosage form is a capsule. In another preferred embodiment according to the present invention, the dosage form is a tablet.

The triple vital bacteria composition according to the present invention can be prepared to various dosage forms by conventional methods. For example, it can be prepared to tablet, capsule and granule and the like by the method disclosed in CN1119145C. For example, 1. a method for preparing capsule: pretreating starting materials and additives; drying powders; mixing and sieving the starting materials and additives; filling capsule; loading into bottle; and loading into box.

2. a method for preparing granule: pretreating starting materials and additives; pelletizing; drying powders; mixing and sieving the starting materials and additives; filling powder; loading bubble cap; loading single and medium box; and loading box.

3. a method for preparing tablet: pretreating starting materials and additives; pelletizing; drying powders; mixing and sieving the starting materials and additives; pressing; internal packing; loading case; and loading box.

EXAMPLES

Preparation of Juice of Tomato

Tomato with fresh color, lucent skin, thick succulence, non-stem, non-stain and non-crack was accurately weighted, the amount or which could be determined according to the practical requirement. The above preliminary-sieved tomato was placed into a pool for washing. The washed tomato was placed into a clean tank. The washed tomato was loaded into a pulverizer in turn and then poured into a heat-sterilizing cooker for sterilization. The juice of tomato after heat-sterilizing was centrifugated to prepare juice of tomato.

Example 1

Preparation of Seed Culture Medium for Inoculating *Bifidobacterium longum*

500 ml of pure water were used to dissolve the glucose (available from Hebei ShenXue Glucose Corporation, China), Yeast powder (available from MERCK KGAA., Germany), ammonium sulfate (available from Jiangsu Yonghua Fine Chemical Corproation, China, AR grade), potassium dihydrogen phosphate (available from Shantou Jinsha Chemical Corporation, China, AR grade), dipotassium hydrogen phosphate (available from Shantou Jinsha Chemical Corporation, China, AR grade) and isolactose (available from INALCO S.P.A., Italy), all having an amount listed in the following table 1, to form a solution, 1500 ml of pure water were used to uniform defatted milk powder (available from FONTERRA LTD., New Zeland) having an amount listed in the following table 1 with refiner (Shanghai Sample Model Factory, DS-1) to form a suspension.

The above solution and suspension were grinded uniformly with colloid mill (available from Wenzhou Lucheng Mulser Corporation, JM-L80), and then were loaded into a seed bottle. Drinking water was added to 4000 g to form a seed culture medium for *Bifidobacterium longum*. A small amount of diluted NaOH solution was added to adjust the pH of the medium.

The above seed bottle was sealed and sterilized in a sterilization tank under 121° C. for 10 to 15 minutes.

TABLE 1

| components | formation of 4000 g | | | | |
| --- | --- | --- | --- | --- | --- |
| | Formation 1 | Formation 2 | Formation 3 | Formation 4 | Formation 5 |
| Defatted milk powder | 44 g | 44 g | 196 g | 260 g | 260 g |
| glucose | 12 g | 12 g | 58 g | 80 g | 80 g |
| Yeast powder | 24 g | 54 g | 54 g | 54 g | 60 g |
| Ammonium sulfate | 3 g | 55 g | 55 g | 55 g | 100 g |
| potassium dihydrogen phosphate | 1 g | 20 g | 12 g | 12 g | 20 g |
| dipotassium hydrogen phosphate | 2 g | 80 g | 43 g | 2 g | 80 g |
| isolactose | 8 g | 40 g | 32 g | 8 g | 40 g |

Example 2

Preparation of Seed Culture Medium for Fermenting *Lactobacillus acidophilus* and *Streptococcus faecalis*

500 ml of pure water were used to dissolve the glucose (available from Hebei ShenXue Glucose Corporation, China), Yeast powder (available from MERCK KGAA., Germany), lactose (available from Shanghai Shenmei Medicine Development Technology Corporation, China) and Juice of tomato (available from Xinxin Store, Jinyang Stree, Pudong District, Shanghai, China), all having an amount listed in the following table 2, to form a solution. 1500 ml of pure water were used to uniform tryptone (available from MERCK KGAA., Germany) and peptone (available from Nippon Medicine Corporation), both having an amount listed in the following table 2 with refiner (Shanghai Sample Model Factory, DS-1) to form a suspension.

The above solution and suspension were grinded uniformly with colloid mill, and then were loaded into a seed bottle. Drinking water was added to 4000 g to form a seed culture medium for *Lactobacillus acidophilus* and *Streptococcus faecalis*. Then, a small amount of diluted sodium hydroxide solution was added to adjust pH of the culture medium.

The above seed bottle was sealed and sterilized in a sterilization tank under 121° C. for 10 to 15 minutes.

TABLE 2

| components | formation of 4000 g | | | | |
| --- | --- | --- | --- | --- | --- |
| | Formation 1 | Formation 2 | Formation 3 | Formation 4 | Formation 5 |
| Juice of tomato | 18 g | 18 g | 500 g | 920 g | 920 g |
| glucose | 6 g | 6 g | 60 g | 100 g | 100 g |
| Yeast powder | 2 g | 43 g | 43 g | 43 g | 80 g |
| tryptone | 40 g | 160 g | 160 g | 160 g | 200 g |
| peptone | 4 g | 60 g | 36 g | 4 g | 60 g |
| lactose | 2 g | 20 g | 13 g | 2 g | 20 g |

Example 3

Preparation of Fermentation Culture Medium for *Bifidobacterium longum*

All of the components other than calcium carbon listed in the following table 3 were placed into a stainless steel barrel, and then 30 kg of drinking water were poured into the stainless steel barrel, while stirring by a stainless steel bar, thereby obtaining a suspension of culture medium. The resultant suspension was poured into a colloid mill to grind uniformly. The grinded suspension was poured into a fermenter with an agitator, and water was added to 400 kg. The agitator of the fermenter was turned on, and NaOH was added to adjust pH of the culture medium. Then, calcium carbon listed in the following table 3 was added, and water was added to 400 kg, thereby obtaining the fermentation culture medium. The fermentation culture medium was sterilized under 121° C. for 10 to 15 minutes.

TABLE 3

| 400 kg of formulation | | | | | |
|---|---|---|---|---|---|
| components | Formulation 1 | Formation 2 | Formation 3 | Formation 4 | Formation 5 |
| Defatted milk powder | 4.4 kg | 4.4 kg | 20 kg | 26 kg | 26 kg |
| Glucose | 2 kg | 2 kg | 9 kg | 12 kg | 12 kg |
| Yeast powder | 2.4 kg | 6.2 kg | 6.2 kg | 6.2 kg | 6 kg |
| Ammonium sulfate | 0.2 kg | 2.3 kg | 2.3 kg | 2.3 kg | 4 kg |
| potassium dihydrogen phosphate | 0.1 kg | 1.1 kg | 1.1 kg | 0.1 kg | 2 kg |
| dipotassium hydrogen phosphate | 0.1 kg | 4 kg | 2.1 kg | 0.1 kg | 4 kg |
| Calcium carbonate | 0.2 kg | 10 kg | 5.3 kg | 0.2 kg | 10 kg |

Example 4

Preparation of Fermentation Culture Medium for *Lactobacillus acidophilus* and/or *Streptococcus faecalis*

All the components other than Juice of tomato listed in the following table 4 were placed into a stainless steel barrel, and then 30 kg of drinking water were poured into the stainless steel barrel, while stirring by a stainless steel bar, thereby obtaining a suspension of culture medium. The resultant suspension was poured into colloid mill to grind uniformly. The grinded suspension was poured into a fermenter with an agitator, and water was added to 40 L. The agitator of the fermenter was turned on, and NaOH was added to adjust pH of culture medium. Then, juice of tomato listed in the following table 4 was added, and water was added to 400 kg, thereby obtaining a fermentation culture medium. The fermentation culture medium was sterilized at 121° C. for 10 to 15 minutes.

TABLE 4

| 400 kg of formulation | | | | | |
|---|---|---|---|---|---|
| components | Formulation 1 | Formation 2 | Formation 3 | Formation 4 | Formation 5 |
| Juice of tomato | 1.8 kg | 1.8 kg | 50 kg | 92 kg | 92 kg |
| glucose | 0.6 kg | 0.6 kg | 6 kg | 10 kg | 10 kg |
| Yeast powder | 0.2 kg | 4.3 kg | 4.3 kg | 4.3 kg | 8 kg |
| tryptone | 4 kg | 16 kg | 16 kg | 16 kg | 20 kg |
| peptone | 0.4 kg | 6 kg | 3.6 kg | 0.4 kg | 6 kg |
| lactose | 0.2 kg | 2 kg | 1.3 kg | 0.2 kg | 2 kg |

Example 5

Preparation of Bacterial Slurry of *Bifidobacterium longum*

40 ml of *Bifidobacterium longum* seed (available from Chinese Biological Detecting Institute) were placed into a 5000 ml glass serum bottle filled with seed culture medium obtained from example 1 (formulations 1-5) and was inoculated at 37.0±2.0° C. Inoculated products A1-A5 are obtained respectively.

The above inoculated products A1-A5 were placed in 600 L fermenting tank (Zhangjiagang Jiangnan Chemical Mechanical Corporation, China) with fermenting culture medium obtained from example 3 (Formulations 1-5). The fermentation was carried out under 37.0±2.0° C. and a pressure of 0.05±0.03 MPa, and fermented products B1-B5 were obtained respectively.

The above fermented products B1-B5 were placed respectively into the centrifuge tube of GQ142 tubular centrifuge available from Shanghai Centrifuge Institute and were centrifugated under normal temperature. The flow rate of the fermenting liquid was adjusted in the range of from 4000 to 9000 ml/min. After centrifugation of 90-150 minutes, the centrifuge tube was removed. Slurries C1-C5 were obtained from the centrifuge tubes and placed to stainless steel barrel.

Example 6

Preparation of Slurry of *Lactobacillus acidophilus*

40 ml of *Lactobacillus acidophilus* seed (available from Chinese Biological Detecting Institute) were placed to a 5000 ml glass serum bottle with seed culture medium obtained from example 2 (formulations 1-5) and were inoculated at 37.0±2.0° C. Inoculated products D1-D5 were obtained respectively.

The above inoculated products D1-D5 were placed in 600 L fermenting tank (Zhangjiagang Jiangan Chemical Mechanical Corporation, China) with fermenting culture medium obtained from example 4 (Formulations 1-5). The fermentation was carried out under 37.0±2.0° C. and a pressure of 0.05±0.03 MPa, and fermented products E1-E5 are obtained respectively.

The above fermented products E1-E5 were placed respectively into a centrifuge tube of GQ142 tubular centrifuge available from Shanghai Centrifuge Institute and were centrifugated under normal temperature. The flow rate of the fermenting liquid was adjusted in the range of from 4000 to 9000 ml/min. After centrifugation of 40-80 minutes, the centrifuge tube was removed. Slurries F1-F5 were obtained from the centrifuge tubes and placed to stainless steel barrel.

Example 7

Preparation of Slurry of *Streptococcus faecalis*

40 ml of *Streptococcus faecalis* seed (available from Chinese Biological Detecting Institute) were placed to a 5000 ml glass serum bottle with seed culture medium obtained from example 2 (formulations 1-5) and were inoculated at 37.0±2.0° C. Inoculated products G1-G5 were obtained respectively.

The above inoculated products G1-G5 were placed in a 600 L fermenting tank (Zhangjiagang Jiangnan Chemical Mechanical Corporation, China) with fermenting culture medium obtained from example 4 (Formulations 1-5). The fermentation was carried out under 37.0±2.0° C. and a pressure of 0.05±0.03 MPa, and fermented products H1-H5 were obtained respectively.

The above fermented products H1-H5 were placed respectively into a centrifuge tube of GQ142 tubular centrifuge available from Shanghai Centrifuge Institute and were centrifugated under normal temperature. The flow rate of the fermenting liquid was adjusted in the range of from 4000 to 9000 ml/min. After centrifugation of 40-80 minutes, the centrifuge tube was removed. Slurries I1-I5 were obtained from the centrifuge tubes and placed to stainless steel barrel.

Example 8

Preparation of Powder of *Bifidobacterium longum*

Slurries C1-C5 obtained from example 5 were added into the protection agents having a composition listed in the following table respectively (in which slurries C1-C5 were respectively added into the protection agents of formulations 1-5). Meanwhile, they were grinded uniformly by colloid mill. The uniform mixtures obtained were placed into a freeze-drying machine (Beijing Tianli Technology, GLZ-6) for freeze-drying. During freeze-drying, the inlet temperature of the plate was cooled for pre-freezing such that the products were pre-frozen to about −40° C. After pre-freezing, condensation was performed to lower the temperature of the cold trap to −40° C. Then an vacuum bump was turned on to vacuum the tank. When the tank vacuum reached the setting point (15 pa), the products were warmed. Once the products had the same color, the freeze-drying was complete, thereby obtaining bacteria powders of J1-J5.

TABLE 5

| components | Formulation 1 | Formulation 2 | Formulation 3 | Formulation 4 | Formulation 5 |
|---|---|---|---|---|---|
| Milk powder | 3 kg | 3.75 kg | 4.5 kg | 6 kg | 7.5 kg |
| Sodium glutamate | 750 g | 900 g | 1.05 kg | 1.2 kg | 1.35 kg |
| Isolactose | 6 kg | 7.5 kg | 5.25 kg | 4.5 kg | 2.7 kg |
| Vc-Na | 750 g | 600 g | 450 g | 300 g | 150 g |
| starch | 4.5 kg | 2.25 kg | 3.75 kg | 3 kg | 3.3 kg |

Example 9

Preparation of *Lactobacillus acidophilus*

Slurries F1-F5 obtained from example 6 were added into the protection agents having a composition listed in the following table respectively (in which slurries F1-F5 were added into the protection agents of formulations 1-5, respectively). Meanwhile, they are grinded uniformly by colloid mill. The uniform mixtures obtained are placed into freeze-drying machine (Beijing Tianli Technology, GLZ-6) for freeze-drying. During freeze-drying, the inlet temperature of the plate was cooled for pre-freezing such that the products were pre-frozen to about −40° C. After pre-freezing, condensation was performed to lower the temperature of the cold trap to −40° C. Then an vacuum bump was turned on to vacuum the tank. When the tank vacuum reached the setting point (15 pa), the products were warmed. Once the products had the same color, the freeze-drying was complete, thereby obtaining bacteria powders of K1-K5.

TABLE 6

| components | Formulation 1 | Formulation 2 | Formulation 3 | Formulation 4 | Formulation 5 |
|---|---|---|---|---|---|
| Milk powder | 1.6 kg | 2 kg | 2.4 kg | 3.2 kg | 4 kg |
| Sodium glutamate | 400 g | 480 g | 560 g | 640 g | 720 g |
| Isolactose | 3.2 kg | 4 kg | 2.8 kg | 2.4 kg | 1.44 kg |
| Vc-Na | 400 g | 320 g | 240 g | 160 g | 80 g |
| starch | 2.4 kg | 1.2 kg | 2 kg | 1.6 kg | 1.76 kg |

Example 10

Preparation of *Streptococcus faecalis*

Slurries I1-I5 obtained from example 7 were added into the protection agents having a composition listed in the following table respectively (in which slurries I1-I5 were added into the protection agents of formulations 1-5, respectively). Meanwhile, they are grinded uniformly by colloid mill. The uniform mixtures obtained are placed into freeze-drying machine (Beijing Tianli Technology, GLZ-6) for freeze-drying. During freeze-drying, the inlet temperature of the plate was cooled for pre-freezing such that the products were pre-frozen to about −40° C. After pre-freezing, condensation was performed to lower the temperature of the cold trap to −40° C. Then an vacuum bump was turned on to vacuum the tank. When the tank vacuum reached the setting point (15 pa), the products were warmed. Once the products had the same color, the freeze-drying was complete, thereby obtaining bacteria powders of L1-L5.

TABLE 7

| components | Formulation 1 | Formulation 2 | Formulation 3 | Formulation 4 | Formulation 5 |
|---|---|---|---|---|---|
| Milk powder | 1.6 kg | 2 kg | 2.4 kg | 3.2 kg | 4 kg |
| Sodium glutamate | 400 g | 480 g | 560 g | 640 g | 720 g |
| Isolactose | 3.2 kg | 4 kg | 2.8 kg | 2.4 kg | 1.44 kg |
| Vc-Na | 400 g | 320 g | 240 g | 160 g | 80 g |
| starch | 2.4 kg | 1.2 kg | 2 kg | 1.6 kg | 1.76 kg |

Example 11

Preparation of Capsule of Triple Vital Bacteria Composition

The components listed in the following table were loaded into multiway mixture (HDA-600, Wenzhou Pharmaceutical Equipment Corporation, China) for mixing 30 minutes to obtain uniform mixtures. Capsule filler (Zhejiang Fuchang Mechanical Corporation, Full-Automatic capsule filler, NJP-2000B) was used to prepare M1-M5 capsules, each of which contained 0.6 million capsules, in which Mi capsule included powder Ji of *Bifidobacterium longum*, powder Ki of *Lactobacillus acidophilus* and powder Li of *Streptococcus faecalis*, and i was an integer from 1 to 5.

TABLE 8

|  | Amount of kg |
|---|---|
| Powder J1-J5 of *Bifidobacterium longum* ($\geq 10 \times 10^8$ CPU/g) | 12.0 kg |
| Powder K1-K5 of *Lactobacillus acidophilus* ($\geq 5.0 \times 10^8$ CPU/g) | 6.0 kg |
| Powder L1-L5 of *Streptococcus faecalis* ($\geq 5.0 \times 10^8$ CPU/g) | 3.0 kg |
| Pre-gelling starch | 52.5 kg |
| lactose | 52.5 kg |

Example 12

Preparation of Powder of Triple Vital Bacteria Composition

The components listed in the following table were loaded into multiway mixture (HDA-600, Wenzhou Pharmaceutical Equipment Corporation, China) for mixing 30-40 minutes to obtain uniform mixtures. Powder filler (Zhejiang Songchuan Packing Mechanical Corporation, multibank packing machine, SL-8) was used to prepare N1-N5 pulvises, each of which contained 0.1 million pulvises, in which Ni included powder Ji of *Bifidobacterium longum*, powder Ki of *Lactobacillus acidophilus* and powder Li of *Streptococcus faecalis*, and i was an integer from 1 to 5.

The control powder is prepared as follows: the components listed in the following table 10 were sprayed and pelletized, and then dried in an oven under 100° C.

TABLE 9

|  | Amount |
|---|---|
| Powder J1-J5 of *Bifidobacterium longum* | 9.2 kg |
| Powder K1-K5 of *Lactobacillus acidophilus* | 4.0 kg |
| Powder L1-L5 of *Streptococcus faecalis* | 2.5 kg |
| Control powder | 82.5 kg |
| Milk solid essence | 0.4 kg |
| Lemon solid essence | 0.1 kg |

TABLE 10

Formulation of control powder of pulvis

|  | Amount |
|---|---|
| Defatted milk powder | 70 kg |
| Malt dextrin | 21 kg |
| Isolactose | 14 kg |
| HPMC(2910) 0.3% | 150 g |
| 95% ethanol | 25 kg |
| water | 25 kg |

Example 13

Stability Test

The following powders of bacteria were packed with aluminum-piastic bag by vacuum, and stored under the corresponding temperatures. The amount of bacteria was determined per month.

| | Storage temperature: 2-8° C. | | |
|---|---|---|---|
| Storage time | J1 | K1 | L1 |
| 0 | $5.7 \times 10^9$ | $7.8 \times 10^9$ | $7.1 \times 10^9$ |
| 3 months | $6.2 \times 10^9$ | $4.5 \times 10^9$ | $6.3 \times 10^9$ |
| 6 months | $4.1 \times 10^9$ | $3.0 \times 10^9$ | $5.0 \times 10^9$ |
| 12 months | $2.1 \times 10^9$ | $3.7 \times 10^9$ | $1.0 \times 10^9$ |
| 24 months | $8.9 \times 10^7$ | $2.4 \times 10^8$ | $1.9 \times 10^8$ |

| | Storage temperature: 2-8° C. | | |
|---|---|---|---|
| Storage time | J2 | K2 | L2 |
| 0 | $6.1 \times 10^9$ | $7.1 \times 10^9$ | $5.9 \times 10^9$ |
| 3 months | $3.1 \times 10^9$ | $7.7 \times 10^9$ | $6.7 \times 10^9$ |
| 6 months | $2.0 \times 10^9$ | $6.7 \times 10^9$ | $3.8 \times 10^9$ |
| 12 months | $9.8 \times 10^8$ | $5.0 \times 10^9$ | $8.8 \times 10^8$ |
| 24 months | $3.0 \times 10^8$ | $1.7 \times 10^8$ | $7.6 \times 10^7$ |

| | Storage temperature: 2-8° C. | | |
|---|---|---|---|
| Storage time | J5 | K5 | L5 |
| 0 | $3.8 \times 10^9$ | $8.2 \times 10^9$ | $7.9 \times 10^9$ |
| 3 months | $4.4 \times 10^9$ | $7.6 \times 10^9$ | $8.0 \times 10^9$ |
| 6 months | $3.0 \times 10^9$ | $3.8 \times 10^9$ | $6.7 \times 10^9$ |
| 12 months | $1.3 \times 10^9$ | $8.7 \times 10^8$ | $7.8 \times 10^8$ |
| 24 months | $1.2 \times 10^8$ | $3.7 \times 10^8$ | $2.0 \times 10^8$ |

| | Storage temperature: 25° C. | | |
|---|---|---|---|
| Storage time | J1 | K1 | L1 |
| 0 | $5.7 \times 10^9$ | $7.8 \times 10^9$ | $7.1 \times 10^9$ |
| 3 months | $6.2 \times 10^9$ | $4.5 \times 10^9$ | $6.3 \times 10^9$ |
| 6 months | $8.2 \times 10^8$ | $1.0 \times 10^9$ | $4.7 \times 10^8$ |
| 12 months | $2.3 \times 10^8$ | $3.2 \times 10^8$ | $1.8 \times 10^8$ |
| 18 months | $7.7 \times 10^7$ | $8.3 \times 10^7$ | $7.8 \times 10^7$ |

| | Storage temperature: 25° C. | | |
|---|---|---|---|
| Storage time | J2 | K2 | L2 |
| 0 | $6.1 \times 10^9$ | $7.1 \times 10^9$ | $5.9 \times 10^9$ |
| 3 months | $3.1 \times 10^9$ | $7.7 \times 10^9$ | $6.7 \times 10^9$ |
| 6 months | $7.7 \times 10^8$ | $8.3 \times 10^8$ | $5.0 \times 10^8$ |
| 12 months | $3.5 \times 10^8$ | $1.9 \times 10^8$ | $2.0 \times 10^8$ |
| 18 months | $8.0 \times 10^7$ | $5.6 \times 10^7$ | $4.7 \times 10^7$ |

| | Storage temperature: 25° C. | | |
|---|---|---|---|
| Storage time | J5 | K5 | L5 |
| 0 | $3.8 \times 10^9$ | $8.2 \times 10^9$ | $7.9 \times 10^9$ |
| 3 months | $4.4 \times 10^9$ | $7.6 \times 10^9$ | $8.0 \times 10^9$ |
| 6 months | $3.9 \times 10^8$ | $5.0 \times 10^8$ | $8.1 \times 10^8$ |
| 12 months | $1.0 \times 10^8$ | $8.8 \times 10^7$ | $1.3 \times 10^8$ |
| 18 months | $5.7 \times 10^7$ | $7.8 \times 10^7$ | $6.7 \times 10^7$ |

| | Storage temperature: 37° C. | | |
|---|---|---|---|
| Storage time | J1 | K1 | L1 |
| 0 | $5.7 \times 10^9$ | $7.8 \times 10^9$ | $7.1 \times 10^9$ |
| 1 month | $1.7 \times 10^9$ | $3.1 \times 10^9$ | $30 \times 10^9$ |
| 2 months | $2.3 \times 10^8$ | $7.8 \times 10^9$ | $6.7 \times 10^8$ |
| 3 months | $1.8 \times 10^8$ | $1.5 \times 10^8$ | $9.7 \times 10^7$ |

| Storage time | Storage temperature: 37° C. | | |
|---|---|---|---|
| | J2 | K2 | L2 |
| 0 | $6.1 \times 10^9$ | $7.1 \times 10^9$ | $5.9 \times 10^9$ |
| 1 month | $8.3 \times 10^8$ | $7.8 \times 10^8$ | $4.6 \times 10^8$ |
| 2 months | $3.0 \times 10^8$ | $4.7 \times 10^8$ | $3.9 \times 10^8$ |
| 3 months | $5.6 \times 10^7$ | $3.7 \times 10^7$ | $4.5 \times 10^7$ |

| Storage time | Storage temperature: 37° C. | | |
|---|---|---|---|
| | J5 | K5 | L5 |
| 0 | $3.8 \times 10^9$ | $8.2 \times 10^9$ | $7.9 \times 10^9$ |
| 1 month | $8.9 \times 10^8$ | $1.1 \times 10^8$ | $9.7 \times 10^8$ |
| 2 months | $1.7 \times 10^8$ | $5.1 \times 10^8$ | $9.8 \times 10^7$ |
| 3 months | $1.1 \times 10^8$ | $5.8 \times 10^7$ | $3.4 \times 10^7$ |

Comparative Examples 1-3

Triple vital bacteria compositions were prepared according to examples 1-3 of CN1119154C, respectively, i.e., comparative examples 1-3. The stabilities of *Bifidobacterium longum*, *Lactobacillus acidophilus* and *Streptococcus faecalis* in the triple vital bacteria compositions from comparative examples 1-3 were determined according to the method in example 13. The results were as follows:

| Storage time | B | L | S |
|---|---|---|---|
| Storage temperature: 2-8° C. (comparative example 1) | | | |
| 0 | $3.3 \times 10^9$ | $3.0 \times 10^9$ | $3.0 \times 10^9$ |
| 3 months | $2.0 \times 10^9$ | $1.7 \times 10^9$ | $2.4 \times 10^9$ |
| 6 months | $5.7 \times 10^8$ | $8.0 \times 10^8$ | $1.0 \times 10^9$ |
| 12 months | $1.0 \times 10^8$ | $4.1 \times 10^8$ | $7.0 \times 10^9$ |
| 24 months | $1.6 \times 10^7$ | $6.0 \times 10^7$ | $1.1 \times 10^7$ |
| Storage temperature: 2-8° C. (comparative example 2) | | | |
| 0 | $1.3 \times 10^9$ | $8.0 \times 10^9$ | $2.0 \times 10^9$ |
| 3 months | $1.0 \times 10^9$ | $6.4 \times 10^9$ | $1.0 \times 10^9$ |
| 6 months | $7.9 \times 10^8$ | $3.7 \times 10^9$ | $9.2 \times 10^8$ |
| 12 months | $3.0 \times 10^8$ | $1.0 \times 10^9$ | $6.5 \times 10^8$ |
| 24 months | $8.8 \times 10^6$ | $1.7 \times 10^7$ | $7.1 \times 10^7$ |
| Storage temperature: 2-8° C. (comparative example 3) | | | |
| 0 | $2.0 \times 10^{10}$ | $1.0 \times 10^{10}$ | $3.1 \times 10^9$ |
| 3 months | $1.0 \times 10^{10}$ | $8.3 \times 10^9$ | $1.0 \times 10^9$ |
| 6 months | $8.0 \times 10^9$ | $5.4 \times 10^9$ | $7.4 \times 10^8$ |
| 12 months | $8.0 \times 10^8$ | $2.0 \times 10^9$ | $4.0 \times 10^8$ |
| 24 months | $3.6 \times 10^7$ | $4.5 \times 10^7$ | $9.0 \times 10^6$ |
| Storage temperature: 25° C. (comparative example 1) | | | |
| 0 | $3.3 \times 10^9$ | $3.0 \times 10^9$ | $3.0 \times 10^9$ |
| 6 months | $5.6 \times 10^8$ | $4.1 \times 10^8$ | $7.0 \times 10^8$ |
| 12 months | $7.2 \times 10^7$ | $8.1 \times 10^7$ | $1.0 \times 10^8$ |
| 18 months | $1.0 \times 10^7$ | $2.6 \times 10^7$ | $5.1 \times 10^7$ |
| Storage temperature: 25° C. (comparative example 2) | | | |
| 0 | $1.3 \times 10^9$ | $8.0 \times 10^9$ | $2.0 \times 10^9$ |
| 6 months | $3.0 \times 10^8$ | $1.0 \times 10^9$ | $7.6 \times 10^8$ |
| 12 months | $5.0 \times 10^7$ | $4.6 \times 10^7$ | $2.3 \times 10^8$ |
| 18 months | $8.6 \times 10^6$ | $1.0 \times 10^7$ | $7.1 \times 10^7$ |
| Storage temperature: 25° C. (comparative example 3) | | | |
| 0 | $2.0 \times 10^{10}$ | $1.0 \times 10^{10}$ | $3.1 \times 10^9$ |
| 6 months | $7.0 \times 10^9$ | $2.8 \times 10^9$ | $5.7 \times 10^8$ |
| 12 months | $2.1 \times 10^8$ | $8.7 \times 10^8$ | $1.0 \times 10^8$ |
| 18 months | $5.6 \times 10^7$ | $4.0 \times 10^8$ | $4.0 \times 10^7$ |
| Storage temperature: 37° C. (comparative example 1) | | | |
| 0 | $3.3 \times 10^9$ | $3.0 \times 10^9$ | $3.0 \times 10^9$ |
| 1 month | $5.7 \times 10^8$ | $8.0 \times 10^8$ | $7.0 \times 10^9$ |
| 2 months | $1.0 \times 10^7$ | $2.3 \times 10^7$ | $1.7 \times 10^7$ |
| 3 months | $6.3 \times 10^6$ | $5.2 \times 10^6$ | $4.7 \times 10^6$ |
| Storage temperature: 37° C. (comparative example 2) | | | |
| 0 | $1.3 \times 10^9$ | $8.0 \times 10^9$ | $2.0 \times 10^9$ |
| 1 month | $6.6 \times 10^8$ | $7.3 \times 10^8$ | $3.7 \times 10^8$ |
| 2 months | $4.5 \times 10^7$ | $6.0 \times 10^7$ | $4.8 \times 10^7$ |
| 3 months | $6.4 \times 10^6$ | $7.0 \times 10^6$ | $5.8 \times 10^6$ |
| Storage temperature: 37° C. (comparative example 3) | | | |
| 0 | $2.0 \times 10^{10}$ | $1.0 \times 10^{10}$ | $3.1 \times 10^9$ |
| 1 month | $8.0 \times 10^9$ | $8.4 \times 10^9$ | $6.0 \times 10^8$ |
| 2 months | $7.1 \times 10^8$ | $6.1 \times 10^8$ | $5.1 \times 10^7$ |
| 3 months | $6.2 \times 10^7$ | $5.9 \times 10^7$ | $7.0 \times 10^6$ |

B represented *Bifidobacterium longum*, L represented *Lactobacillus acidophilus* and S represented *Streptococcus faecalis*.

Example 14

Application of Triple Vital Bacteria Compositions

Patients suffering from functional were orally administrated with M1 from example 11 thrice per day, with one capsule at each time. The results are as follows:

1) Results on Efficiency

This test included 141 samples. The result showed that the number of defecation per day of the patients suffering from functional constipation was increased to 0.63 times per day from (0.30, 0.35) times per day before treatment, after the patients were administrated of capsule M1 for one month, p<0.0001. After two weeks of treatment, Week Bristol Subtype Mean was greatly improved (from 0.61, 0.63 to 1.76), P<0.0001.

Estimate on effect to by-pass symptom of constipation: after treatment of one month, the effective rate of improvement of the by-pass symptom of constipation was 46.2%, and 81.5% after treatment of 3 months.

The analysis on the improvement to single symptom showed that the integral on single symptom was greatly reduced after administration of capsule M1 for one month (P<0.05).

The analysis on the total integral improvement to conventional symptom of constipation showed that the total integral was greatly reduced after administration of capsule M1 for one month (P<0.001).

2) The Result on Safety: No Adverse Reaction

Example 15

Application of Triple Vital Bacteria Composition

This example showed the effect of the triple vital bacteria composition according to the present invention on diarrhea.

A. Selection Criteria for Patients
1. Adult Acute Diarrhea
(1) Mild or common acute diarrhea:
*Mild—patients had a body temperature below 38° C. and un-obvious clinical symptom, and suffered from diarrhea for no more than 4-5 times/day; feces was in pulpy shape; no visible purulent discharge could be observed; culture of feces showed negative.

*Common—patients had a temperature around 38-39° C. and the number of leucocytes was below 20,000/ml; there was purulent or mucus discharge and diarrhea 5-15 times/day, with mucus or pus and blood; patients remained full conscious with normal cardiovascular and respiratory functions; patients did not have somnolent and convulsion symptom.

(2) Acute diarrhea with unclear cause (including bacteroidal and viral); patients had detrimental eating and drinking habit; the disease occurred abruptly; patients had diarrhea for more than 3 times/day; there was no purulent discharge; the number of leucocytes was below 15 as determined by microscope under high powder field.

2. Adult Chronic diarrhea: patients had diarrhea for 2-3 times/day; the shape of feces were abnormal for 2-3 months; the disease appeared repeatedly and appeared recently again.

3. Adult Constipation: patients suffered from constipation and defecated only once for 2-3 days; the feces were dry and hard; patients had trouble in defecation and often needed laxative suppository or lubricant; the constipation had lasted for more than one week.

4. Infant Acute and Chronic diarrhea with various causes (infectivity or non-infectivity) or $0^+$-13 years old outpatients or inpatients having constipation.

B. Design of the Clinical Trials:
The patients stopped to use any other drugs (antibiotics, hormone, other antidiarrheal or agents for moisturizing the intestine) before treatment, and were administrated with capsules M2 obtained from example 12. The doses were as follows: 2-3 times/day with 5 capsules at each time for adult; 3 times/day with one capsule at each time for $0^+$-1 year old children; 3 times/day with 2 capsules at each time for 1-6 years old children; 3 times/day with 3 capsules at each time for 6-13 years old children. Data obtained from the clinical trials were processed statistically according to chi-square test and Ridit analysis.

C. Results of the Clinical Trials
1. 401 patients suffering from adult or children mild or mid acute diarrhea and chronic diarrhea with unknown causes were administrated with capsule M2 according to example 12. The total efficacy was 87.5%. In addition, the effect of capsule M2 on acute diarrhea is better than that on chronic diarrhea (these two effects had a significant difference, $P<0.05$). Total effective rates for acute diarrhea of adult and children were 92.3% and 90.7%, respectively. And the total effective rates for chronic diarrhea were 80.0% and 76.3%, respectively.

2. In addition to treating diarrhea caused by unknown reasons, the capsule M2 was also effective in treating infectious diarrhea caused by dysentery bacteria, salmonellae, pathogenic coliform bacteria, jejunum curved bacteria, pseudomonas aerogened and rotavirus and the like. In 401 patients, 52 patients were determined as being infected by pathogens (bacteria class) and 8 patients were infected by rotavirus before treatment. 50 of the 52 patients (96.2%) were turned to negative after treatment. And all 8 patients infected by rotavirus were effective after treatment.

3. Although the effect of capsule M2 on chronic diarrhea was not better than that on acute diarrhea, capsule M2 was indeed effective on chronic diarrhea. The patients suffering from chronic diarrhea had been administrated by other drugs before trial, which did not produce any obvious effect, or was diagnosed as Irritable bowel syndrome for a long time. After administration of capsule M2, 80.0% of adult and 76.3% of children were cured.

4. Capsule M2 was effective in regulating intestinal flora. From the detection results obtained before and after treatment of 19 adults and 16 children suffering from diarrhea, it could be found that, before treatment, patients were suffered from abnormal intestinal flora to a certain extent. The main symptoms included that the numbers of enteric bacilli, aerobic or facultative anaerobic bacteria were too high and the number of anaerobic bacteria such as *Bifidobacteria* was too low. After treatment, as the clinical symptoms vanished, the above conditions were improved and the intestinal flora of these patients was recovered to normal condition.

5. Capsule M2 has no side efects.

What is claimed is:
1. A triple vital bacteria composition, including consisting of:
    powder of *Bifidobacterium longum*,
    powder of *Lactobacillus acidophilus*, and
    powder of *Streptococcus faecalis*,
    wherein the powder of *Bifidobacterium longum* consists of *Bifidobacterium longum* and a first protection agent, wherein the first protection agent consists of 8-50% of defatted milk powder, 0.01-10% of sodium glutamate, 8-50% of isolactose, 0.01-5% of Vc-Na and 5-30% of starch, based on a total weight of the first protection agent,
    wherein the powder of *Lactobacillus acidophilus* consists of *Lactobacillus acidophilus* and a second protection agent and the powder of *Streptococcus faecalis* consists of *Streptococcus faecalis* and the second protection agent, and the second protection agent consists of 6-70% of defatted milk powder, 0.01-10% of sodium glutamate, 8-50% of isolactose, 0.01-5% of Vc-Na and 4-30% of starch, based on a total weight of the second protection agent.

2. A method for preparing the triple vital bacteria composition of claim 1, comprising the following steps:
    (a) inoculating *Bifidobacterium longum* in a first seed culture medium to obtain an inoculated product of *Bifidobacterium longum*;
    (b) inoculating *Lactobacillus acidophilus* in a second seed culture medium to obtain an inoculated product of *Lactobacillus acidophilus*;
    (c) inoculating *Streptococcus faecalis* in the second seed culture medium to obtain an inoculated product of *Streptococcus faecalis*;
    (d) fermenting the inoculated product of *Bifidobacterium longum* obtained from step (a) in a first fermenting culture medium to obtain a fermented product of *Bifidobacterium longum*;
    (e) fermenting the inoculated product of *Lactobacillus acidophilus* obtained from step (b) in a second fermenting culture medium to obtain a fermented product of *Lactobacillus acidophilus*;
    (f) fermenting the inoculated product of *Streptococcus faecalis* obtained from step (c) in the second fermenting culture medium to obtain a fermented product of *Streptococcus faecalis*;
    (g) mixing *Bifidobacterium longum* with a first protection agent and then freeze-drying to obtain powder of *Bifidobacterium longum*;
    (h) mixing *Lactobacillus acidophilus* and *Streptococcus faecalis* with a second protection agent, respectively and then freeze-drying to obtain powder of *Lactobacillus acidophilus* and powder of *Streptococcus faecalis*; and (i) mixing the above powder of *Bifidobacterium longum*, powder of *Lactobacillus acidophilus* and powder of *Streptococcus faecalis* to obtain a triple vital bacteria composition, wherein the first protection agent consists of 8-50% of defatted milk powder, 0.01-10% of sodium glutamate, 8-50% of isolactose, 0.01-5% of Vc-Na and 5-30% of starch, based on a total weight of the first protection agent, wherein the second protection agent consists of 6-70% of defatted milk powder, 0.01-10% of sodium glutamate, 8-50% of isolactose, 0.01-5% of Vc-Na and 4-30% of starch, based on a total weight of the second protection agent.

3. The method according to claim 2, wherein the first seed culture medium comprises 1.1-6.5% by weight of nitrogen source, 0.5-3% by weight of carbon source, 0.6-1.5% by weight of nutritious material, 0.15-5% by weight of mineral salt and 84.00-97.65% by weight of solvent.

4. The method according to claim 2, wherein the second seed culture medium comprises 1.1-6.5% by weight of nitrogen source, 0.2-3% by weight of carbon source, 0.5-25% by weight of nutritious material, and 65.5-98.2% by weight of solvent.

5. The method according to claim 2, wherein the first fermenting culture medium comprises 1.1-6.5% by weight of nitrogen source, 0.5-3% by weight of carbon source, 0.6-1.5% by weight of nutritious material, 0.15-5% by weight of mineral salt and 84.00-97.65% by weight of solvent.

6. The method according to claim 3, the second fermenting culture medium comprises 1.1-6.5% by weight of nitrogen source, 0.2-3% by weight of carbon source, 0.5-25% by weight of nutritious material, and 65.5-98.2% by weight of solvent.

7. A method of treating constipation comprising administrating a patient in need thereof an effective amount of the triple vital bacteria composition according to claim 1.

8. The triple vital bacteria composition of claim 1, wherein the *Bifidobacterium longum* in the powder of *Bifidobacterium longum* is at least $10 \times 10^8$ CPU/g, the *Lactobacillus acidophilus* in the powder of *Lactobacillus acidophilus* is at least $5.0 \times 10^8$ CPU/g, and the *Streptococcus faecalis* in the powder of *Streptococcus faecalis* is at least $5.0 \times 10^8$ CPU/g.

9. The triple vital bacterial composition of claim 8, wherein the total weight of the first protection agent is different from the total weight of the second protection agent.

* * * * *